US005747054A

United States Patent [19]

Yang et al.

[11] Patent Number: 5,747,054
[45] Date of Patent: May 5, 1998

[54] COMPOSITIONS OF GYPSUM PESTICIDE BRIQUETS

[76] Inventors: Kim W. Yang, 4124 Rainsong Dr., Dallas, Tex. 75287; George J. Junginger, 1609 Homestead St., Flower Mound, Tex. 75028; Raymond G. Mockridge, 4104 Bentley Ct., Grapevine, Tex. 76051; Robert C. Pearce, III, 3218 Kenilworth Dr., Arlington, Tex. 76017

[21] Appl. No.: 28,103

[22] Filed: Mar. 8, 1993

[51] Int. Cl.⁶ .................................................. A01N 25/08
[52] U.S. Cl. ............................ 424/409; 424/408; 424/84
[58] Field of Search ............................... 424/408, 409, 424/84

[56] References Cited

U.S. PATENT DOCUMENTS

| 1,457,321 | 6/1923 | Strong | 424/409 |
| 4,876,091 | 10/1989 | Clark, Jr. | 424/421 |
| 4,971,796 | 11/1990 | Sjogren | 424/417 |
| 5,224,601 | 7/1993 | Gouge et al. | 206/524.7 |

*Primary Examiner*—Neil S. Levy
*Attorney, Agent, or Firm*—Lynn Marcus-Wyner; Michael P. Morris; Melvyn M. Kassenoff

[57] ABSTRACT

Plaster formulations of agricultural and pest control chemicals which form slow release briquets in situ.

13 Claims, No Drawings

COMPOSITIONS OF GYPSUM PESTICIDE BRIQUETS

The present invention concerns a slow release pest control formulation.

More particularly, the invention relates to a gypsum based pesticide which may be produced in situ.

U.S. Pat. No. 4,876,091 and EP Publication 259,806 describes gypsum based insecticidal pellets for use in controlling aquatic insect pests.

U.S. Pat. No. 4,732,762 also describes gypsum based pesticidal compositions, particularly when formed in a regular shape such as a briquet.

U.S. Pat. No. 4,971,796 describes alternative proteinaceous slow release insecticidal compositions.

Each of these references describes the problem of pest and in particular mosquito control and the subject matter thereof in this respect is incorporated herein by reference.

U.S. Pat. No. 4,670,039 describes a gypsum based slow release form of fertilizer.

One of the more common and successful slow release forms of this type is that of the gypsum based briquet as described in U.S. Pat. No. 4,732,762 and marketed under the name Altosid® Briquet. Unfortunately, whilst effective in insect control certain aspects in the manufacture and handling of the briquet can pose problems of an economic and quality control nature. For example one method of manufacture involves preparing a mix of active ingredient, plaster of paris, plaster set accelerator, water and any further additives which may be desired and pouring this into individual briquet molds for setting. Such a manual process is very slow and very costly. There is considerable waste both when pouring into the molds and when removing and further processing the briquets. The products are also dusty and their moisture content is hard to control. Containers become soggy and poor shelf life presents packaging problems. It is often necessary to warm the hardened briquets to remove excess water not required for hardening which again is costly and time consuming.

It has now been found that these problems may be avoided by pre-mixing the dry ingredients and placing this free-flowing pre-mix into a water soluble container e.g. a pouch or capsule which when placed in water will slowly dissolve allowing the gradual addition of water to the pre-mix which will then set in the desired form. This solidified form can then be employed in the usual manner to provide for the controlled continuous release of pesticide e.g. insecticide at the desired locus.

(The term "pouch" is conveniently used herein to describe all such forms according to the invention involving containment of the premix in a water soluble receptacle.)

As will be appreciated such pouched pre-mixes may be placed directly at the locus where aquatic pests are to be controlled for in situ formation of the hardened form or used in manufacture for later use by dipping in water and recovering the hardened briquet. Dissolution of the water soluble outer retaining layer will permit the gradual entry of water and hardening of the plaster.

When used in pre-manufacturing procedures the system according to the invention is fast, reduces waste, provides a water free environment that enhances chemical stability of the active ingredient and eliminates the need for drying.

The pouches or the like can be formed in conventional form-fill-seal such as those produced by Cloud Corporation (Des Plaines, Ill.) or other machines used in the formation of such packaging to a desired size or shape in conventional manner. Application of vacuum or pressure enables the reduction of air pockets and voids in the pouch. The adaptability provided by varying types of plaster with accelerators and retarders and surface active agents as well as polymers with varying solubilities and the ability to manipulate them in varying thicknesses permits extensive and reliable "fine tuning" of desired end forms.

Preferred water settable powders used in preparing the pest control formulation are gypsum based substances such as those based on calcium sulfate hemi-hydrate ($CaSO_4 \cdot \frac{1}{2}H_2O$) and known variously as plaster, molding plaster and plaster of paris. Production of such plasters from gypsum, their properties and various uses are described in Kirk-Othmer, Encyclopedia of Chemical Technology, 3rd ed (1978) v. 4 p 437 ff the contents of which in this respect are incorporated herein by reference.

These plasters revert to calcium sulfate dihydrate ($CaSO_4 \cdot 2H_2O$) and harden when exposed to or mixed with water. The time required for hardening can be controlled through the addition of retarders or accelerators over a range of from ca 4 minutes to ca 8 hours depending on the particular use. High compression plaster having a density of at least 1600 g/liter and compressive strength of at least 5000 p.s.i. is an example of plaster suitable for use due to its slow decomposition in the environment once hardened. (The term "plaster" is used herein collectively for the various forms of calcium sulfate hemi-hydrate described above.) Plaster will typically form between 50 and 95% of the anhydrous premix.

Plasters are available in a variety of grades with respect to purity, set time, expansion rate and solubility and choice of a suitable grade will be readily determinable by one of ordinary skill in the art using routine testing. Examples of commercial suppliers of plaster include USG Corp. (Chicago, Ill.) and Stauffer Chemical Inc. (Westport, Conn.).

Water soluble packaging suitable for formation of the intended pouch includes any substance which will gradually dissolve to permit contact of the premixed formulation with water. Examples are cellulosic materials such as paper, and especially water soluble polymers such as those based on polyvinylalcohol (PVA), cellulose based polymers, starch polymers, acrylic polymers or other such like water soluble polymers or combinations thereof.

Typically the thickness of the material will range from 2 to 25 mil depending on polymer and desired dissolution rate. A dissolution rate of >60 mins is generally preferred as this allows more opportunity for the water to fully penetrate the dry premix. Material may also be used which is caustic resistant.

The active ingredient can be any which is usefully applied by slow release into a damp or more usually aquatic environment to control pests such as insects, fungi, algae, snails, weeds and the like.

Examples of such insecticides, fungicides, molluscicide, herbicides, algicides and the like are given e.g. in U.S. Pat. No. 4,732,762 and U.S. Pat. No. 4,225,693 the contents of which in this respect are incorporated herein by reference.

Preferred active ingredients are insecticides particularly those active against mosquitos, blackfly, midges and other aquatic insect pests. Examples of suitable such insecticides include malathion, carbaryl, naled, insect growth regulators such as methoprene, hydroprene and kinoprene, chitin inhibitors such as seem oil extracts and diflubenzuron, organophosphates e.g. chlorpyrifos, dichlorvos, dimethoate, diazinon, temephos, disulfoton carbamates such as methomyl, and biological insecticides such as those based on *Bacillus thuringiensis* (B.t.) spp e.g. *B.t. israelensis* (e.g. TEKNAR® insecticide). These may be included as active ingredient or in preformulated form or for example in the form of microcapsules.

Examples of other active ingredients which may also be suitable for use in the practice of the invention depending on the target insects include 2-chloro-N-[[[3,5-dichloro-4-[3,4,5-trichloro-1-pyrazolyl]phenyl]amino]carbonyl]benzamide, (cf U.S. Pat. No. 4,950,678 the contents of which are incorporated herein by reference) propetamphos, fluvalinate, fluphenacur, cyromazine, chlorfluazuron, fenoxycarb, diflubenzuron, flucycloxuron, hexaflumuron, teflubenzuron, flufenoxuron, triflumuron, pyriproxyfen, chlorpyrifos ethyl, chlorpyrifos methyl, cypermethrin, lambda-cyhalothrin, cyfluthrin, fenvalerate, esfenvalerate, deltamethrin, fenpropathrin, bifenthrin, permethrin, ethofenprox, tralomethrin, alpha-cypermethrin, bendiocarb, RH 5849 (Rohm & Haas), flucycloxuron, flucythrinate, pyrethrins, allethrin, prallethrin, furethrin, acrinathrin, cyhalothrin, cyphenothrin, phenothrin, resmethrin, tefluthrin, tetramethrin, dimethrin, fenfluthrin, flumethrin, pyresmethrin, terallethrin, tralocythrin, cycloprothrin, synergized pyrethrin and the like.

The active ingredients methoprene, hydroprene and kinoprene bear an asymmetric carbon atom and, accordingly, there are (R) and (S) enantiomers of these compounds. As used herein "(R,S)" refers to the racemic mixture and "(S)" refers to the compound comprising a predominance of the (S)–(+) enantiomer. Where the compound name is used herein without reference to its enantiomeric content, the term is inclusive of both (R,S) and (S) forms.

As mentioned, the premix may contain further additives such as accelerators or retarders or wetting agents and other adjuvants e.g. to assist the environmental stability, particle size, strength, release characteristics and the like of the hardened forms. Typically accelerators or retarders include buffering agents, acids and bases. As a rule these are pre-incorporated in commercially available plaster products which are sold i.a. according to their speed of set. Wetting agents of all kinds (nonionic, anionic, cationic and amphoteric) will assist water in penetrating the premix to facilitate the uniformity of the hardening process.

Other adjuvants include finely divided carbon, swelling bentonite, silicon dioxide, UV stabilizers and the like and emulsifiers such as alkylphenol polyether alcohols.

The dry pre-mix is prepared by mixing the various ingredients in a suitable mixer such as e.g. a turbolizer (Material Processing Corp., Elmhurst, Ill.), roller bottle or the like and if necessary ground to a desired particle size. The pre-mix is then placed into the desired form of package using conventional machines such as Cloud Corporation form-fill-seal machines, AccuRate (Whitewater, Wis.) dry feeders, Acrison (Moonachie, N.J.) dry solids feeders and Tecweigh (St. Paul, Minn.) volumetric/gravimetric feeders.

The release characteristics of the hardened products will depend on the ingredients chosen and can be tailored to the desired use and promised release for example from between 25 to 150 days. The desired degree of buoyancy required of the hardened products for their intended use can also be selected by appropriate choice of ingredients according to their known properties. For example in the control of aquatic insects it is preferred that the product be fully immersed whereas for control of molluscs, especially water snails, the product should remain at or directly below the surface of the water. A more detailed description of pests to be controlled application regimes and ingredients suitable for achieving these is given in U.S. Pat. No. 4,732,762 the contents of which in this respect are incorporated herein by reference.

EXAMPLE 1

A mixture comprising 20 g of (S)-methoprene, 0.5 g of BHT (2,6-di-tert-butyl-4-cresol; Eastman Kodak, Rochester, N.Y.), 0.1 g of propyl gallate (Eastman Kodak, Rochester, N.Y.) 39.4 g of Darco G-60 (charcoal; American Norit; Atlanta, Ga.), 140 g of Hydrocal X-21 (plaster; USG Corp., Chicago, Ill.) and 20 g of Volclay FD-181 (swelling Bentonite; American Colloid; Arlington Heights, Ill.) is packaged dry in a water soluble pouch made of QSA 2000 (PVA film; Air Products Corp; Allentown, Pa.) and tightly compressed and sealed. Upon placing the pouch in a beaker of cold water a solid briquet forms of the same strength and hardness as a conventional pre-molded briquet.

EXAMPLE 2

A mixture is prepared with the ingredients specified in Example 1 and additionally 4 g of Triton X-100 (octylphenoxypolyoxy ethanol; Rohm & Haas Co., Philadelphia, Pa.) and treated in the same way. In this case a solid briquet again forms having the same strength and hardness as a conventional pre-molded briquet.

What is claimed is:

1. A pesticide formulation comprising a water settable powder mixed with a pesticidally effective amount of at least one active ingredient in a water soluble receptacle.

2. A formulation according to claim 1 wherein the water settable powder is a gypsum based substance.

3. A formulation according to claim 1 wherein the active ingredient is an insecticide.

4. A formulation according to claim 3 wherein the active ingredient is an insecticide active against mosquitoes, blackfly, midges and/or other aquatic insect pests.

5. A formulation according to claim 3 wherein the active ingredient is methoprene.

6. A method of forming a pesticidal briquet which comprises placing a water soluble receptacle containing a water settable powder mixed with a pesticidally effective amount of at least an active ingredient in an aquatic environment.

7. A method according to claim 6 which is carried out at the locus where pests are to be controlled.

8. A pesticidal briquet prepared according to claim 6.

9. A pesticidal briquet prepared according to claim 7.

10. A method of combatting pests which comprises applying to the locus thereof a briquet according to claim 8.

11. A method of combatting pests which comprises applying to the locus thereof a briquet according to claim 9.

12. A method according to claim 10 wherein the pests are aquatic.

13. A method according to claim 11 wherein the pests are aquatic.

* * * * *